US012708774B2

(12) United States Patent
Vrabec et al.

(10) Patent No.: US 12,708,774 B2
(45) Date of Patent: Aug. 18, 2026

(54) SUBTHRESHOLD DIRECT CURRENT (DC) NERVE CONDUCTION BLOCK AFTER SUPRATHRESHOLD "PRIMING"

(71) Applicant: Case Western Reserve University, Cleveland, OH (US)

(72) Inventors: Tina L Vrabec, Cleveland, OH (US); Laura Shaw, Cleveland, OH (US); Kevin L. Kilgore, Cleveland, OH (US); Niloy Bhadra, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 72 days.

(21) Appl. No.: 16/957,762

(22) PCT Filed: Dec. 28, 2018

(86) PCT No.: PCT/US2018/067813
§ 371 (c)(1),
(2) Date: Jun. 25, 2020

(87) PCT Pub. No.: WO2019/133784
PCT Pub. Date: Jul. 4, 2019

(65) Prior Publication Data

US 2021/0060344 A1 Mar. 4, 2021

Related U.S. Application Data

(60) Provisional application No. 62/688,446, filed on Jun. 22, 2018, provisional application No. 62/611,095, filed on Dec. 28, 2017.

(51) Int. Cl.
*A61N 1/36* (2006.01)
*A61N 1/04* (2006.01)
(Continued)

(52) U.S. Cl.
CPC ....... *A61N 1/36164* (2013.01); *A61N 1/0456* (2013.01); *A61N 1/0502* (2013.01);
(Continued)

(58) Field of Classification Search
CPC ...... A61N 1/0456; A61N 1/0502; A61N 1/20; A61N 1/36164; A61N 1/36034; A61N 1/36146; A61N 1/36167
See application file for complete search history.

(56) References Cited

U.S. PATENT DOCUMENTS 5,755,750 A 5/1998 Petruska et al.
2011/0160798 A1* 6/2011 Ackermann, Jr. .... A61L 31/048 607/46
(Continued)

FOREIGN PATENT DOCUMENTS

WO WO-2009058258 A1 * 5/2009 ........... A61N 1/0551
WO 2009/061813 A1 7/2010
(Continued)

OTHER PUBLICATIONS

PCT International Search Report and Written Opinion for corresponding International Application Serial No. PCT/US2018/067813, mailed Mar. 27, 2019, pp. 1-13.
(Continued)

*Primary Examiner* — Michael J Carey
(74) *Attorney, Agent, or Firm* — Dinsmore & Shohl LLP

(57) ABSTRACT

A DC nerve conduction block can be maintained by delivering a subthreshold direct current (DC) after priming a neural structure with a suprathreshold DC. A waveform generator can provide a DC waveform including a first phase with a first amplitude capable of providing a nerve conduction block of a neural structure within 1 second and a second phase with a second amplitude less than the first amplitude. One or more electrodes can deliver the first phase for to the
(Continued)

neural structure for a first time to provide the nerve conduction block of the neural structure within 1 second and deliver the second phase to the neural structure for a second time to maintain the block of the neural structure. By maintaining the DC nerve conduction block with the subthreshold DC, significant power can be saved, resulting in an extended battery life of the waveform generator.

19 Claims, 9 Drawing Sheets

(51) Int. Cl.
*A61N 1/05* (2006.01)
*A61N 1/20* (2006.01)

(52) U.S. Cl.
CPC ........... *A61N 1/20* (2013.01); *A61N 1/36034* (2017.08); *A61N 1/36146* (2013.01); *A61N 1/36167* (2013.01)

(56) References Cited

U.S. PATENT DOCUMENTS

2016/0101286 A1* 4/2016 Bhadra ................ A61N 1/3615 607/46
2016/0144175 A1* 5/2016 Simon ................ A61N 1/36021 607/46
2017/0095667 A1* 4/2017 Yakovlev ............. A61B 5/0022
2018/0280691 A1* 10/2018 Ackermann ............. A61N 1/20

FOREIGN PATENT DOCUMENTS

WO WO-2017044542 A1 * 3/2017 ........... A61N 1/0456
WO WO-2018075473 A1 * 4/2018 ........... A61N 1/0504

OTHER PUBLICATIONS

Rizzo, M. A., et al. “Prevalence and treatment of spasticity reported by multiple sclerosis patients.” Multiple Sclerosis Journal 10.5 (2004): 589-595.
Amatya, Bhasker, et al. “Non pharmacological interventions for spasticity in multiple sclerosis.” Cochrane database of systematic reviews 2 (2013).
Lundstrom, Erik, et al. “Four-fold increase in direct costs of stroke survivors with spasticity compared with stroke survivors without spasticity: the first year after the event.” Stroke 41.2 (2010): 319-324.
Naples, Gregory G., et al. “A spiral nerve cuff electrode for peripheral nerve stimulation.” IEEE transactions on biomedical engineering 35.11 (1988): 905-916.
Baron, Ralf. “Neuropathic pain: a clinical perspective.” Sensory Nerves. Springer, Berlin, Heidelberg, 2009. 3-30.
Tiede, Jeffrey, et al. “Novel spinal cord stimulation parameters in patients with predominant back pain.” Neuromodulation: Technology at the Neural Interface 16.4 (2013): 370-375.
Stokvis, Annemieke, J. Henk Coert, and Johan W. van Neck. “Insufficient pain relief after surgical neuroma treatment: Prognostic factors and central sensitisation.” Journal of plastic, reconstructive & aesthetic surgery 63.9 (2010): 1538-1543.
Koch, Horst, et al. “Treatment of painful neuroma by resection and nerve stump transplantation into a vein.” Annals of plastic surgery 51.1 (2003): 45-50.
Franke, M., et al. “Chronic bladder control post SCI via electric KHFAC pudendal nerve block.” Proc. IEEE Embs Conf. Neural Eng.. 2013.
Lin, Yin-Tsong, et al. “Dual-channel neuromodulation of pudendal nerve with closed-loop control strategy to improve bladder functions.” J Med Biol Eng 34.34 (2014): 82-9.
IP Australia Examination Report No. 1 for Application No. 2023200544, Applicant name: Case Western Reserve University, dated May 21, 2024, pp. 1-4.

* cited by examiner

SUBTHRESHOLD DIRECT CURRENT (DC) NERVE CONDUCTION BLOCK AFTER SUPRATHRESHOLD "PRIMING"

RELATED APPLICATION

This application claims priority to U.S. Provisional Application Ser. No. 62/611,095, filed Dec. 28, 2017, entitled "SINE SUBTHRESHOLD BLOCK WITH COMPLETE BLOCK PRIMING", and to U.S. Provisional Application Ser. No. 62/688,446, filed Jun. 22, 2018, entitled "SINE SUBTHRESHOLD BLOCK WITH COMPLETE BLOCK PRIMING". The entireties of these applications are hereby incorporated by reference for all purposes.

GOVERNMENT SUPPORT

This invention was made with government support under R01-NS-089530 and R01-EB-024680 awarded by the National Institutes of Health. The government has certain rights in the invention.

TECHNICAL FIELD

The present disclosure relates generally to nerve conduction block and, more specifically, to systems and methods that deliver a subthreshold direct current (DC) nerve conduction block after priming with a suprathreshold DC.

BACKGROUND

Many neurological diseases are characterized by unwanted neural activity conducted within neural tissue (e.g., along peripheral axons) and inducing pathological effects (e.g., within an end organ). The application of an electrical field to neural tissue has been shown to produce an electrical block of such conduction of neural activity within the neural tissue. Kilohertz frequency alternating current (KHFAC), for example, can produce a steady state depolarization in the neural tissue, leading to KHFAC nerve conduction block. Although KHFAC nerve conduction block has been widely explored and appeared promising, it has not been adopted clinically due to the production of an undesirable onset response in the nerve. While it is possible to completely neutralize the onset response by applying a brief direct current (DC) waveform through a flanking electrode, nerve conduction is lost after several applications of the DC waveform.

DC has become an attractive candidate that can be used for achieving nerve conduction block. Indeed, application of a DC alone can provide either depolarization or hyperpolarization (depending on the polarity of the signal) and produce a complete nerve conduction block without the onset response of the KHFAC nerve conduction block. Additionally, anodic break excitation at cessation can be prevented by the design of the DC nerve conduction block waveform. Therefore, DC is generally the preferred way to deliver the nerve conduction block. The effectiveness of the DC nerve conduction block depends on the magnitude of the electrical field that is applied to the nerve. The lowest electrical field that results in a functional block of the nerve is referred to as the "block threshold", which varies for different neural tissues. Recent experiments have shown that when a block is applied at a block threshold for a prolonged period of time, there is a delay in the recovery of the response. For many applications, it would be advantageous to have instantaneous recovery.

SUMMARY

The present disclosure relates generally to nerve conduction block and, more specifically, to systems and methods that deliver a subthreshold direct current (DC) nerve conduction block after priming with suprathreshold DC. Advantageously, the subthreshold DC nerve conduction block, when the neural tissue is primed with the suprathreshold DC, maintains the nerve conduction block, while accelerating recovery. Additionally, the subthreshold DC requires less power, resulting in a power savings, thereby extending the battery device of the waveform generator.

In an aspect, the present disclosure can include a system that can deliver a DC nerve conduction block. The system includes a waveform generator to provide a direct current (DC) waveform including a first phase with a first amplitude capable of providing a nerve conduction block of a neural structure within 1 second and a second phase with a second amplitude less than the first amplitude. One or more electrodes to deliver the first phase for a first time to provide the nerve conduction block of the neural structure within 1 second and the second phase for a second time to maintain the block of the neural structure.

In a further aspect, the present disclosure can include a method for delivering a DC nerve conduction block. A waveform generator can configure a first phase of a DC waveform with a first amplitude capable of providing a nerve conduction block of a neural structure within one second. The first phase of the DC waveform can be delivered through one or more electrodes for a first time to provide the nerve conduction block of the neural structure. The waveform generator can configure a second phase of the DC waveform with a second amplitude less than the first amplitude. The second phase of the DC waveform can be delivered through the one or more electrodes for a second time to maintain the nerve conduction block of the neural structure.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
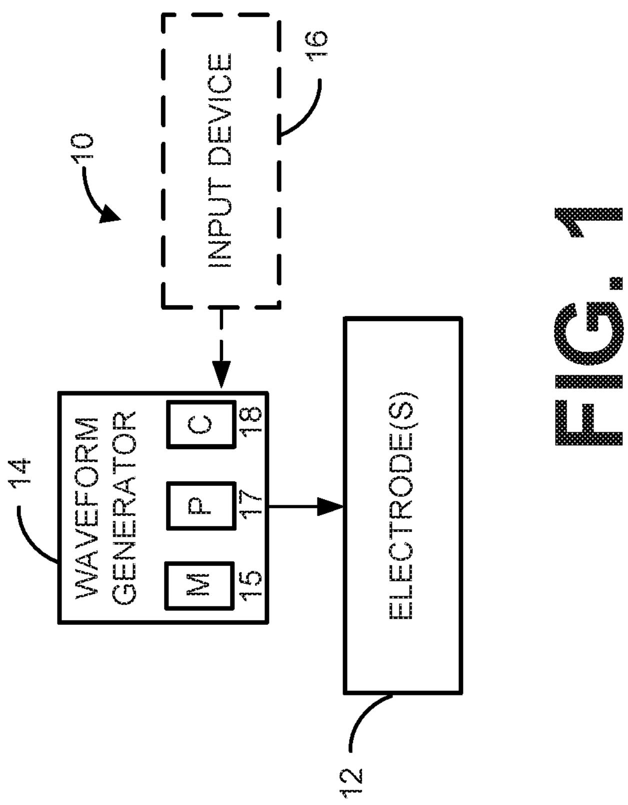
FIG. 1 is a diagram showing a system that can deliver a direct current (DC) nerve conduction block with near instantaneous recovery in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the terms "nerve conduction block" and "block" can refer to the attenuation of conduction in neural tissue due to a change in the electric field caused by application of an electrical signal to the nerve. Attenuating conduction can refer to extinguishing 100% or less (e.g., 90%, 80%, 70%, 60%, 50%, or the like) of the action potentials traveling through the target neural tissue. In one example, when nerve conduction is attenuated, a target nerve will have an increased activation threshold and thereby make the target nerve more difficult to excite. In another example, the conduction velocity within the target nerve can be decreased when nerve conduction is attenuated.

As used herein, the term "electrode" refers to a conductor through which electricity enters or leaves an object, substance, or region. The electrode can be a surface/transcutaneous electrode, a percutaneous electrode, a subcutaneous electrode (e.g., a nerve cuff), or the like.

As used herein, the term "separated interface nerve electrode (SINE)" can refer to an electrode design in which an electrode is separated from a neural structure by a column of electrolyte. The SINE uses ionic coupling, which separates the electron flow and the ionic flow. Because the reactants of the electrochemical reaction are separated from the neural structure, the damaging electrochemical reaction products are separated from the neural structure. Accordingly, the SINE provides a less harmful way to deliver direct current (DC) to tissue to perform nerve conduction block.

As used herein, the term "nerve cuff" refers to an electrode design in which two or more contacts are included in a housing that surrounds a neural structure (e.g., a nerve). One example of a nerve cuff is a carbon ink cuff electrode (which can include platinum foil contacts coated with carbon ink to increase charge capacity).

As used herein, the terms "direct current" or "DC" can refer to a unidirectional flow of electric charge. In some instances, the DC can have a plateau of a cathodic polarity or an anodic polarity. The DC can further be represented as a waveform that includes a ramp from a zero position to the plateau. In some instances, the waveform can also include a ramp down from the plateau position to the zero position. In still other instances, the waveform can include a subsequent plateau of the opposite polarity (in such cases, the waveform can be a biphasic waveform with the second phase configured to reduce charge either as a charge balanced waveform or a charge imbalanced waveform). The waveform can also include ramps from zero to the plateau and/or from the plateau to zero.

As used herein, the term "direct current block" or "DC block" can refer to the application of a direct current pulse with a polarity configured depolarization or hyperpolarization to cause change in the electric field sufficient to alter conduction in the nerve.

As used herein, the terms "alter" or "altering", when used with reference to nerve conduction, can refer to affecting or changing a manner in which action potentials are conducted in a neural structure. In some instances, conduction can be altered by extinguishing an action potential at some point as it travels along the nerve (also referred to as "blocking" conduction). In other instances, conduction can be altered by increasing the activation threshold and/or decreasing the conduction velocity (also referred to as "attenuating" conduction).

As used herein, the terms "block threshold" and "threshold" can refer to the lowest amplitude value of a DC at which a nerve conduction block occurs within 30 seconds of application.

As used herein, the term "suprathreshold" can refer to an amplitude value greater than or equal to the block threshold.

As used herein, the term "subthreshold" can refer to an amplitude value less than the block threshold.

As used herein, the term "priming" can refer to preparing a neural structure for nerve conduction block.

As used herein, the terms "neural tissue" and "neural structure" can refer to tissue related to the central nervous system, peripheral nervous system, autonomic nervous system, and enteric nervous system. The term neural tissue or neural structure, in some instances, can include one or more nerves and/or neural fibers.

As used herein, the term "nerve" can refer to one or more fibers that employ electrical and chemical signals to transmit information. A nerve can refer to either a component of the central nervous system or the peripheral nervous system. For example, in the peripheral nervous system a nerve can transmit motor, sensory, autonomic, and/or enteric information from one body part to another.

As used herein, the term "neurological disorder" can refer to a condition or disease characterized at least in part by abnormal conduction in one or more nerves. The neurological disorder can be in the motor system, the sensory system, and/or the autonomic system.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "medical professional" can refer to an individual who provides care to a patient. A medical professional can be, for example, a doctor, a physician's assistant, a student, a nurse, a caregiver, or the like.

II. Overview

The present disclosure relates generally to nerve conduction block due to the application of an electrical field to one or more neural structures. Direct current (DC) is generally the preferred way to deliver nerve conduction block applications because application of the DC alone can provide either depolarization or hyperpolarization (depending on the polarity of the DC signal) and produce a complete conduction block (depending on the magnitude of the DC signal) without producing an onset response and the DC waveform can be configured to avoid anodic break excitation at cessation. However, when a DC is applied at a block threshold (providing the lowest electrical field that results in a functional block of conduction within the neural structure) for a prolonged period of time, there is a delay in the recovery of the response. For many applications, it would be advantageous to have instantaneous recovery.

Such instantaneous recovery can be achieved by applying the DC in a different way. The present disclosure relates, more specifically, to systems and methods that deliver a subthreshold DC nerve conduction block of a neural structure after priming the neural structure with a suprathreshold DC. A waveform generator can generate a first phase of a DC waveform with the suprathreshold amplitude to provide a nerve conduction block of a neural structure within 1 second and a second phase of the DC waveform with a subthreshold amplitude. One or more electrodes can deliver the first phase for to the neural structure for a first time to provide the nerve conduction block of the neural structure within 1 second and deliver the second phase to the neural structure for a second time to maintain the block of the neural structure. By maintaining the DC nerve conduction block with the subthreshold DC, significant power can be saved, extending the battery life of the waveform generator.

III. Systems

One aspect of the present disclosure can include a system 10 (FIG. 1) that can deliver a direct current (DC) nerve conduction block with near instantaneous recovery of conduction after the DC is shut off. While DC is generally the preferred way to deliver nerve conduction block, when a DC is applied at a block threshold (providing the lowest electrical field that results in a functional block of conduction within the neural structure) for a prolonged period of time, there is a delay in the recovery of conduction. For many applications, it would be advantageous if the recovery of conduction happened more quickly, ideally instantaneously. The system 10 provides a mechanism for the near instantaneous recovery—by initiating the DC nerve conduction block with a first suprathreshold phase of a DC waveform and maintaining the DC nerve conduction block with a second subthreshold phase of the DC waveform.

The system 10 can include a waveform generator 14 to configure the DC waveform coupled to one or more electrodes 12 (including a source electrode and a return electrode) to deliver the DC waveform to a neural structure to achieve the nerve conduction block. In one example, the neural structure can be a peripheral nerve (e.g., motor, sensory, and/or autonomic/enteric) or a nerve or nervous tissue comprising the central nervous system (e.g., brain and/or spinal cord). The DC nerve conduction block can be used to treat various neurological disorders including, but not limited to, chronic neuropathic pain or muscle spasticity. The DC nerve conduction block can also be used to modulate or inhibit neural activity in the autonomic or enteric system. Additionally, the DC nerve conduction block can be used to manage regional applications, like chronic headache management or bladder control.

The waveform generator 14 can be implantable and/or external to a patient's body. Additionally, the waveform generator 14 can include a power source, which can be a battery (such as a rechargeable battery), line power, or the like. The power source can provide power to one or more of a non-transitory memory (M) 15, a processor (P) 17, or circuitry (C) 18. In some instances, the coupling of the waveform generator 14 to each of the one or more electrodes 12 can be via a wired connection (e.g., via an external wire, a percutaneous wire or a subcutaneous wire). In other instances, the coupling of the waveform generator 14 to the one or more electrodes 12 can be via a wireless connection (e.g., the electrodes are inductively powered, the electrodes have their own power source and/or other components, etc.). In still other instances, the coupling of the waveform generator 14 to the one or more electrodes 12 can be via a connection that is both wired and wireless.

The waveform generator 14 can be any device configured or programmed to configure, generate, and deliver (to the electrode(s) 12) the specified one or more DC waveforms for application to the target neural tissue to achieve an alternation in conduction thereof. One example of a waveform generator 14 is a battery-powered, portable generator (the waveform generator 14 positioned externally). Another example of a waveform generator 14 is an implantable generator (IPG) (at least a portion of the waveform generator 14 positioned subcutaneously). It will be appreciated that the waveform generator 14 can include additional components to selectively configure the current waveform, such as an amplitude modulator (not shown).

The waveform generator 14 can configure the one or more DC waveforms with at least two phases: a first suprathreshold phase and a second subthreshold phase. To do so, the waveform generator 14 can determine a block threshold (which may be an anodic value or a cathodic value) based on the neural structure being blocked and/or the application the block is being used for. For example, the waveform generator can have information stored in the non-transitory memory 15 related to the block threshold of different neural structures. As another example, the waveform generator 14 can receive an input (e.g., from an input device 16, which can permit manual input or automatic input) corresponding to the block threshold. It should be noted that the first suprathreshold phase and the second subthreshold phase can be generated at sequentially or with a gap between the generation of the first suprathreshold phase and the second subthreshold phase. The first suprathreshold phase and the second subthreshold phase can be configured (e.g., by the processor 17 and/or the circuitry 18) with certain amplitudes (based on the block threshold) and times (with the time the first suprathreshold phase applied being less than the time the second subthreshold pulse is applied).

The first suprathreshold phase of the DC waveform can have an amplitude greater than or equal to the block threshold. The second subthreshold phase of the DC waveform can have an amplitude less than the block threshold (as low as possible to maintain the block of the neural structure). For example, the subthreshold phase of the DC waveform can have an amplitude between 0 and 99% of the suprathreshold phase of the DC waveform. As another example, the subthreshold phase of the DC waveform can have an amplitude less than or equal to 95%, 90%, 85%, 80%, 75%, 70%, 65%, 60%, 55%, 50%, 45%, 40%, 35%, 30%, 25%, 20%, 15%, 10%, 5% of the suprathreshold phase of the DC waveform. The subthreshold amplitude can reduce the power consumption of the waveform generator 14 compared to the power that would be consumed if the first suprathreshold amplitude were applied at for the same time as the first suprathreshold phase and the second subthreshold phase are applied. In some instances, a reversing phase can be applied after the second subthreshold phase combined.

Figure 2:
FIG. 2 is a schematic diagram of a separated interface nerve electrode (SINE) that can be used by the system in FIG. 1.
Figure 2:
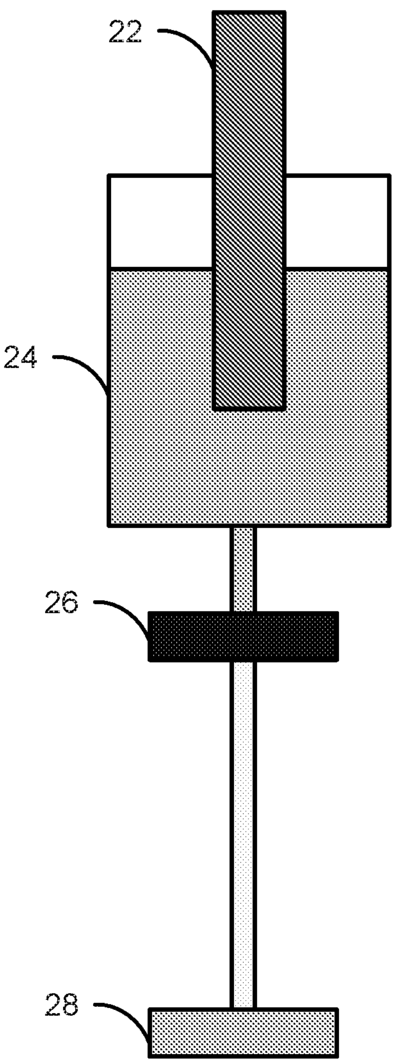

The waveform generator 14 can send the DC with the first suprathreshold phase and the second subthreshold phase to one or more electrodes 12 (source electrodes) for delivery of the DC conduction block to the neural structure. For example, the one or more source electrodes can include a separated interface nerve electrode (SINE) 20, as illustrated in FIG. 2. The SINE separates a metal electrode 22 from a neural interface 28 by an electrolyte 24 and a stopper 26 to confine any reaction products away from the neural structure. The neural interface 28 used with the SINE can be a surface/transcutaneous electrode, a percutaneous electrode, and/or a subcutaneous electrode. The one or more electrodes 12 can also include a return electrode, which can be a unique electrode placed remote from the source electrodes, part of the waveform generator 14, or the like.

The first suprathreshold phase can be delivered to the neural structure through the source electrodes for the first time to provide the nerve conduction block to the neural structure. The first suprathreshold pulse can establish a nerve conduction block in the neural structure within 1 second. The first suprathreshold pulse can be applied for the first time determined by the waveform generator 14. Then, the second subthreshold pulse can be delivered to the neural structure through the source electrodes for the second time to maintain the nerve conduction block. The second subthreshold pulse, in some instances, can immediately follow the first suprathreshold pulse. However, in other instances, a delay (e.g., less than 100 ms, such as 95, 90, 85, 80, 75, 70, 65, 60, 55, 50, 45, 40, 35, 30, 25, 20, 15, 10, or 5 ms) can occur between the suprathreshold pulse and the subthreshold pulse. The second subthreshold pulse can be applied for a second time determined by the waveform generator (although not strictly necessary, the second time can be longer than the first time). In one example, the first suprathreshold pulse can be applied for 60 seconds and the second subthreshold pulse can be applied for 600 seconds. When the second subthreshold phase is shut off, the neural structure can recover in an accelerated fashion, so that conduction is restored nearly instantaneously (e.g., any value from 0 to 500 s; such as, less than 500 s, 400 s, 300 s, 200 s, 100 s, 50 s, 25 s, 15 s, 10 s, 5 s, or 0 s).

In some instances, one or more of the first suprathreshold phase and the second subthreshold phase can be modified according to an input from an input device 16. The input device 16 can provide a manual input and/or an automatic input to the waveform generator 14 related to a modification of the first suprathreshold phase and/or the second subthreshold phase that is desired to be made. For example, when the input device 16 provides the automated response, the input device 16 can be a hardware controller that includes a non-transitory memory and a processor. In this example, the hardware controller can be a simple proportional controller or a sophisticated feedback controller that uses a model configured to estimate at least one dynamic system property. The dynamic system property can be of the neural structure, the one or more DC waveforms, and/or the one or more electrodes 12.

IV. Methods

Another aspect of the present disclosure can include a method 30 (FIG. 3) for delivering a DC nerve conduction block with instantaneous recovery. The method 40 of FIG. 4 extends the method 30 and illustrates an example of configuring the DC nerve conduction block according to an input. The methods 30 and 40 can be executed using the system 10 shown in FIG. 1 and described above.

The methods 30 and 40 are illustrated as process flow diagrams with flowchart illustrations. For purposes of simplicity, the methods 30 and 40 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40.

Figures 3, 4:
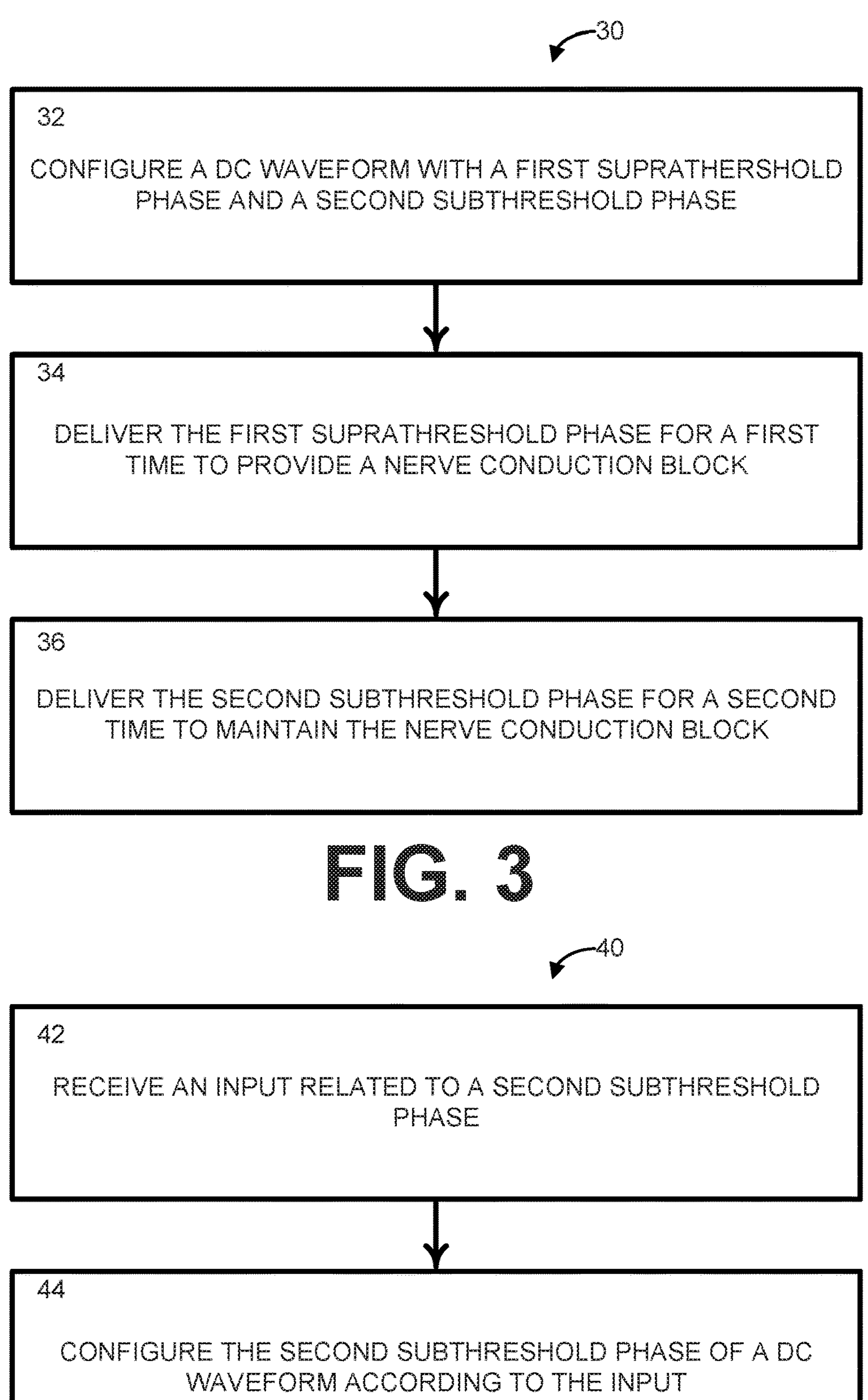
FIG. 3 is a process flow diagram illustrating a method for delivering a DC nerve conduction block with near instantaneous recovery according to another aspect of the present disclosure.
FIG. 4 is a process flow diagram illustrating a method for configuring the DC nerve conduction block of FIG. 3 according to an input.

Referring now to FIG. 3, illustrated is a method 30 for delivering a DC nerve conduction block with instantaneous recovery. The DC nerve conduction block, in some instances, can be a complete block. In other instances, the DC nerve conduction block can be a partial block.

At Step 32, one or more direct current (DC) waveforms can be configured (e.g., by waveform generator 14) with a first suprathreshold phase and a second subthreshold phase. The first suprathreshold phase and the second subthreshold phase can be generated sequentially or after a break in time between the generations. The first suprathreshold phase and the second subthreshold phase can be configured with certain amplitudes (based on the block threshold) and times. The block threshold can be an anodic or cathodic value that is determined based on the neural structure targeted for DC nerve conduction block. In some examples, the neural structure can be a peripheral nerve or neural fibers (e.g., motor, sensory, enteric, and/or autonomic) or a nerve or nervous tissue comprising the central nervous system (e.g., brain and/or spinal cord). The first suprathreshold phase of the DC waveform can have an amplitude greater than or equal to the block threshold. The second subthreshold phase of the DC waveform can have an amplitude less than the block threshold (as low as possible to maintain the block of the neural structure). For example, the subthreshold phase of the DC waveform can have an amplitude between 0 and 99% of the suprathreshold phase of the DC waveform. As another example, the subthreshold phase of the DC waveform can have an amplitude less than or equal to 95%, 90%, 85%, 80%, 75%, 70%, 65%, 60%, 55%, 50%, 45%, 40%, 35%, 30%, 25%, 20%, 15%, 10%, 5% of the suprathreshold phase of the DC waveform. The subthreshold amplitude can reduce the power consumption of the waveform generator compared to the power that would be consumed if the first suprathreshold amplitude were applied at for the same time as the first suprathreshold phase and the second subthreshold phase combined.

At Step 34, the first suprathreshold phase can be delivered to the neural structure through one or more electrodes (e.g., electrode(s) 12) for the first time to provide the nerve conduction block to the neural structure. The first suprathreshold pulse can establish a nerve conduction block in the neural structure within 1 second. At Step 36, the second subthreshold pulse can be delivered to the neural structure through the one or more electrodes (e.g., electrode(s) 12) for the second time to maintain the nerve conduction block. When the second subthreshold phase is shut off, the neural structure can recover in an accelerated fashion, so that conduction is restored nearly instantaneously (e.g., any value from 0 to 500 s; such as, less than 500 s, 400 s, 300 s, 200 s, 100 s, 50 s, 25 s, 15 s, 10 s, 5 s, or 0 s).

The one or more electrodes can be configured to deliver the first suprathreshold pulse and the second subthreshold pulse transcutaneously, percutaneously, or subcutaneously. In some instances, the one or more electrodes can include at least one separated interface nerve electrode (SINE). A portion of the SINE contacting a metal electrode can be filed with high surface area carbon to create a slurry, which can increase the charge capacity of the SINE. For example, the SINE confines reaction products close to the electrode so monophasic DC waveforms can be delivered to the nerve.

FIG. 4 gives an example 40 of configuring the DC nerve conduction block according to an input. In this example, the second subthreshold phase can be configured; however, the first suprathreshold phase can also be configured similarly. At Step 42, an input related to the second subthreshold phase can be received. The input can be related to the subthreshold amplitude or the time the second subthreshold phase is delivered. Additionally, in some instances, the input can be a manual input, but in other instances, the input can be automated (e.g., by a controller device, such as a proportional controller or a feedback controller that estimates dynamic system properties, with a non-transitory memory and a processor that can provide autonomous, automatic control (without requiring user intervention)). At Step 44, the second subthreshold pulse of the DC waveform can be configured according to the input. In some instances, the second subthreshold pulse of the DC waveform can be reconfigured according to the input as the second subthreshold pulse is being delivered.

V. Experimental

The following experiment shows the use of a subthreshold direct current (DC) nerve conduction block after priming with a suprathreshold DC. The "priming" technique can be used to increase the amount of block that can be achieved at subthreshold values while reducing the amount of recovery time needed to restore function to the neural tissue. The decrease in recovery time would allow the nerve conduction block to remain on for a longer period of time while still having nearly instant recovery.

The following experimental results are shown for the purpose of illustration only and are not intended to limit the scope of the appended claims.

Methods

Experimental Setup

Figure 5:
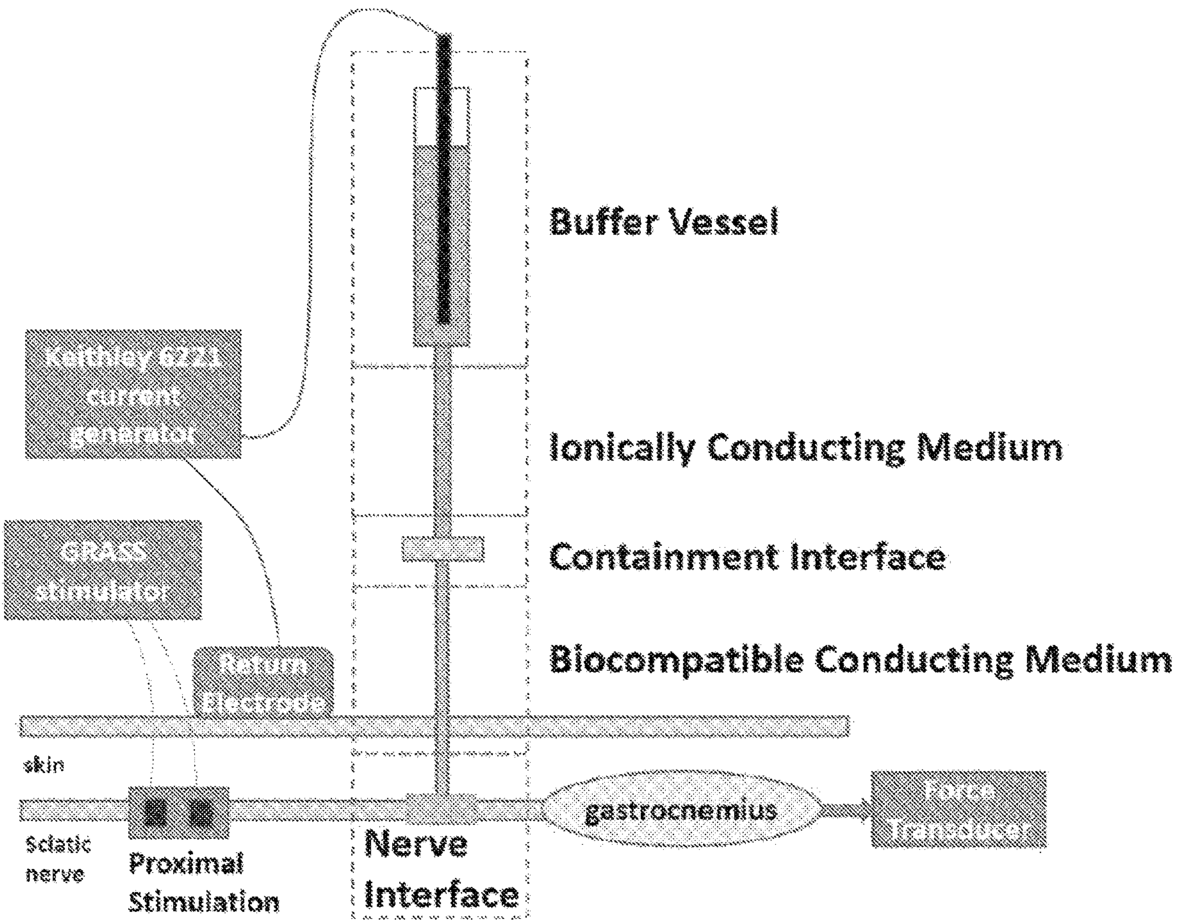
FIG. 5 is an example illustration of an experimental setup using a separated interface nerve electrode (SINE) for a DC block application.

In vivo experiments were performed on five Sprague-Dawley rats using a separated interface nerve electrode (SINE) (an example of which is shown in FIG. 5). The SINE electrode physically separates the metal electrode and the nerve cuff interface by a column of electrolyte. Any reactions that occur at the metal electrode are contained in the electrolyte.

To improve charge capacity, the electrolyte was a high surface area carbon/saline "slurry". To improve the capacity of the SINE electrode, high surface area carbon (YP-50) was added to the saline to form a stiff paste. All of the carbon in the paste was electrochemically available for capacitive (double-layer) charging. A syringe filter prevented the carbon from leaching out into the electrolyte connection down to the nerve. A silicone cuff interfaced to the nerve.

A current-controlled Keithley current generator provided the DC waveform for the DC nerve conduction block. A proximal stimulation electrode was placed on the sciatic nerve. The blocking electrode was applied 1 mm distally through a separate incision. The gastrocnemius tendon was instrumented for force recordings.

In Vivo Testing

Block threshold was defined as the lowest value at which complete block occurred within 30 seconds of application. The block threshold was determined at the start of each experiment.

Tests performed were the block percentage test and the priming test. The block percentage test determined the amount of block at subthreshold values by taking a percentage of the block threshold. The priming test included setting the current output to the block threshold for 60 seconds. The output was then transitioned to one of three subthreshold values for 10 minutes. The percentage of block as determined by the force was recorded throughout. The order of subthreshold testing was randomized in sets of three. The block was maintained for 10 minutes and then the amount of time for an initial force twitch was recorded.

Results

Block Percentage Test

Figure 6:
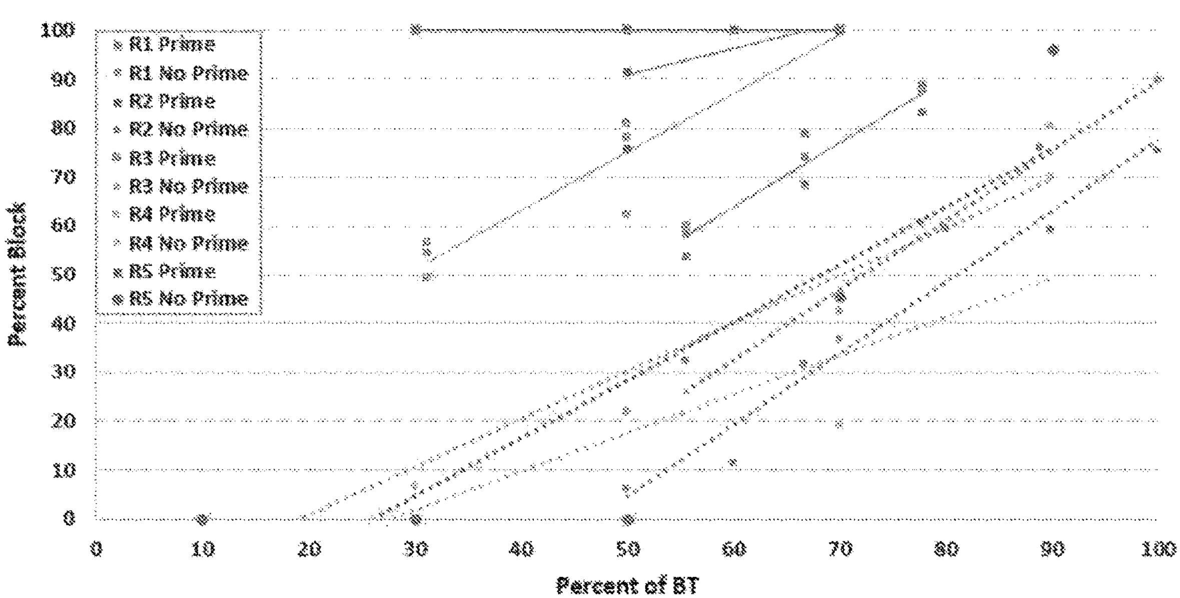
FIG. 6 is a plot showing a percent block achieved for five animals versus a percent of a block threshold of an applied DC.

Blocking Percentage—For all five animals, the percentage of block increased during the subthreshold application when initial 60 second period of complete block at the block threshold were applied (as shown in FIG. 6). In two animals, the use of the priming technique resulted in complete block for a tested subthreshold values. The block thresholds ranged from −0.8 mA to −5.0 mA.

Figure 7:
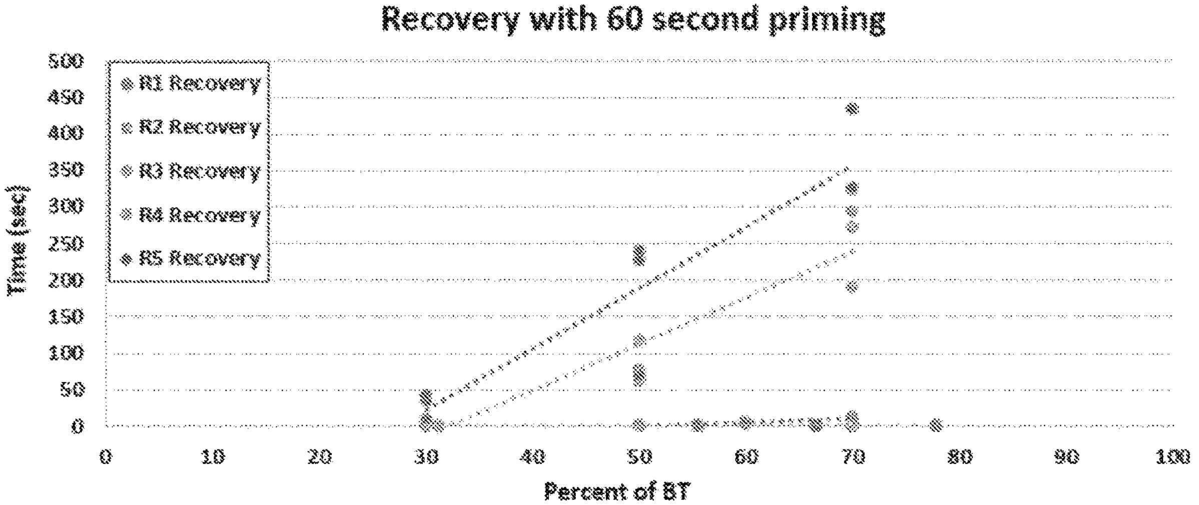
FIG. 7 is a plot showing recovery time with a percent of a block threshold of an applied DC.

Recovery (shown in FIG. 7)—For the three animals that did not have complete block in all trials, the recovery time period was reduced below 15 seconds for all trials. For the two animals with complete block, the amount of time needed for recovery increased as the subthreshold value used increased.

Priming Test

Figure 8:
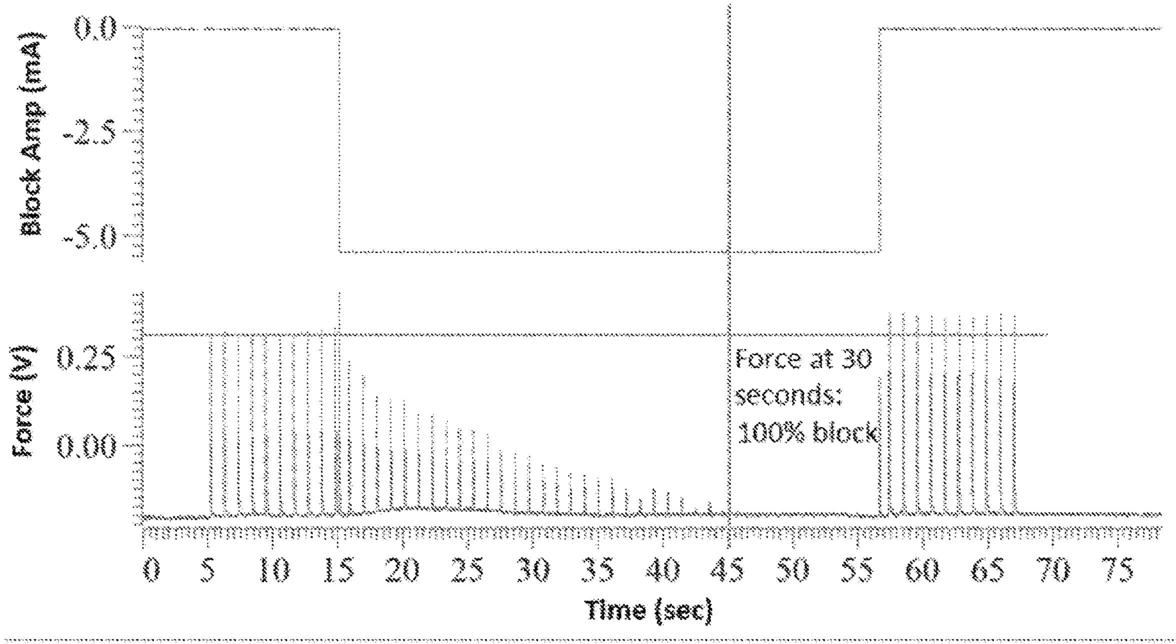
FIG. 8 is a plot showing the force of the gastrocnemius tendon when a DC is applied at a block threshold.
Figure 9:
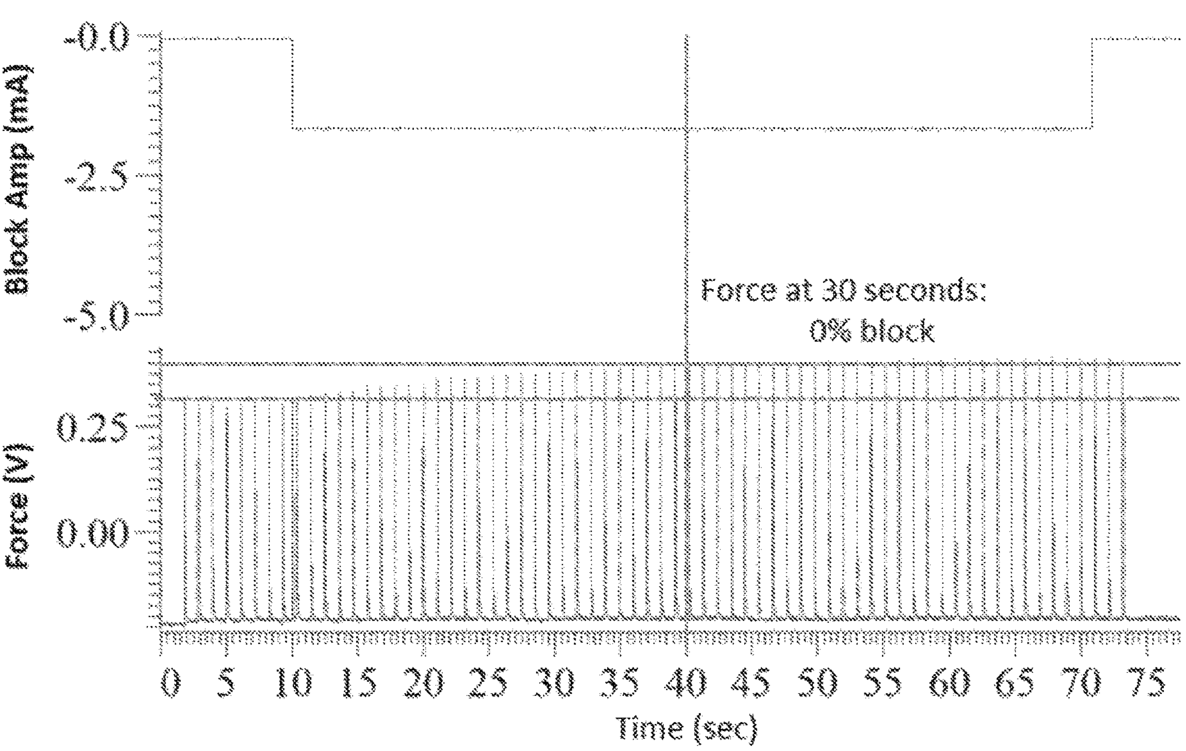
FIG. 9 is a plot showing the force of the gastrocnemius tendon when a DC is applied at 30% of block threshold.
Figure 10:
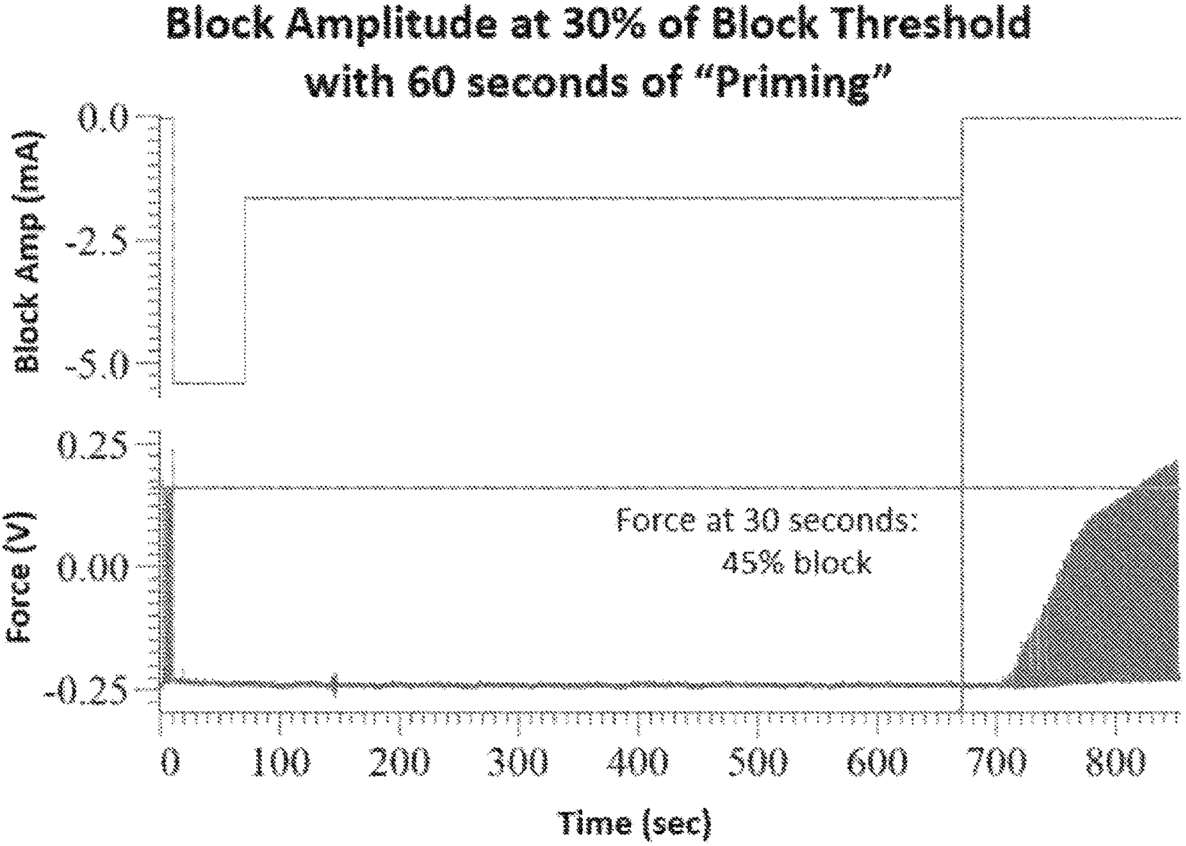
FIG. 10 is a plot showing the force of the gastrocnemius tendon when a DC is applied at 30% of block threshold after a priming with a DC at the block threshold.

At block threshold, the force drops to zero within 30 seconds of the application of block (−5.0 mA) (shown in FIG. 8). For a block amplitude of 30% of the block threshold (−1.5 mA), no block occurs within 30 seconds (shown in FIG. 9), which is considered to be a zero percent block. As shown in FIG. 10, when a 60 second priming at the block threshold (−5.0 mA) is applied, the force goes to zero. When the output is then set to the 30% subthreshold value (1.5 mA), the force remained at zero for 10 minutes. When the block is turned off, recovery begins within 15 seconds.

VI. Examples

Direct current (DC) nerve conduction block is fast acting, reversible, onset free, and easy to modulate, making it ideal for a variety of applications in a patient's nervous system. Although previous studies have investigated DC block as an implantable solution, many applications would be served by a solution that consumes less power than traditional solutions by maintaining the DC block with a subthreshold DC after priming with a suprathreshold DC.

It will be appreciated that the DC nerve conduction block can be applied to one or more neural structures related to the central nervous system, peripheral nervous system, autonomic nervous system, and enteric nervous system. However, described below are certain examples of some of the various medical conditions for which DC nerve conduction block can be used. The following examples are for the purpose of illustration only not intended to limit the scope of the appended claims.

Motor System

In the motor system, spasticity is a debilitating condition that is a result of many different neurological conditions. A few examples of such neurological conditions include cerebral palsy, multiple sclerosis, spinal cord injury and stroke. In each example, the onset of spasticity results in many impairments and limitations including, but not limited to, gait disorders, fatigue, restricted range of movement, abnormal limb postures, quality of life issues, problems with activities of daily living, and/or pain, all of which impact the patient's quality of life. In addition to the quality of life impact of spasticity, the economic burden of any neurological condition increases significantly at the onset of spasticity. For stroke, it has been demonstrated that spasticity causes a four-fold increase in the direct costs associated with treating stroke patients. DC nerve conduction block can provide a solution that can minimize spasticity while maintaining muscle tone allowing for previously unattainable functional improvements.

Sensory System

In the sensory system, chronic neuropathic pain would be an ideal target for DC nerve conduction block. Neuropathic pain follows trauma or disease affecting the peripheral or central nervous system. Examples of such trauma can include physical trauma, spinal cord injury, while examples of such disease can be a side effect of chemotherapy, radiation, or surgery.

With some peripheral neuropathic pain, the source of the pain is localized at a neuroma. As is common with amputations, when a peripheral nerve is damaged, the peripheral nerve tries to regenerate itself towards the distal target. If the distal target is unavailable, axon sprouts grow into the surrounding scar tissue forming a neuroma, which can cause chronic pain and hypersensitivity. A neuroma is particularly well suited to DC nerve conduction block given the local nature of the condition. Also, the electrode used for DC nerve conduction block can easily be removed and placed in a different location, making the DC nerve conduction block desirable in the event that the neuroma changes in a way that lessens the effect of the nerve block.

Autonomic System

In the autonomic system, the properties of DC nerve conduction block provide a unique opportunity for modulation of neural activity. The autonomic nervous system frequently operates around a baseline of neural activity, which is modulated up or down to produce the desired physiological effects. For example, blood pressure is maintained through tonic activity in the autonomic nervous system. It would be extremely beneficial to not only be able to enhance neural activity, but also to inhibit neural activity in a graded/modulated manner. Direct current can be modulated to affect a sub-population of axons to achieve a graded response. In the autonomic system, the onset response is particularly confounding since the effect is prolonged due to the dynamics of the system. The ability to produce an onset free nerve block is absolutely critical to provide an effect solution to autonomic diseases.

Regional Applications

Some regional applications are well suited to DC nerve conduction block intervention. As an example, damage to the occipital nerve can result in chronic headache symptoms. Pharmacological nerve blocks, which are often used to treat this condition, could easily be replaced with a minimally invasive DC nerve conduction block, which would provide a longer term relief. As another example, the pudendal nerve has successfully been blocked using KHFAC and nerve cuff electrodes for bladder control. Both of these methods could be enhanced by less invasive solution. Also, the DC would be capable of providing smooth transitions between partial and complete block which could further improve the functionality of the application.

From the above description, those skilled in the art will perceive improvements, changes and modifications. Such improvements, changes and modifications are within the skill of one in the art and are intended to be covered by the appended claims.

The following is claimed:

1. A method for accelerating a recovery time of a neural structure after ending a conduction block of the neural structure with only a direct current waveform having at least two phases, the method comprising:

providing a first phase of the direct current waveform from a waveform generator to one or more electrodes, the first phase of the direct current waveform having a first amplitude that provides the conduction block of the neural structure, wherein the first amplitude is a block threshold value for the neural structure;

delivering the first phase of the direct current waveform through the one or more electrodes to the neural structure for a first time to provide the conduction block;

providing a second phase of the direct current waveform from the waveform generator to the one or more electrodes, the second phase of the direct current waveform having a second amplitude less than the first amplitude but non-zero, wherein the second amplitude is a subthreshold value for the neural structure;

delivering the second phase of the direct current waveform through the one or more electrodes to the neural structure for a second time, after the first time, to maintain the conduction block of the primed neural structure; and shutting off the second phase of the direct current waveform after the second time, wherein the recovery time of the primed neural structure is accelerated when the second phase of the direct current waveform is shut off compared to when only the first phase of the direct current waveform is delivered, wherein the one or more electrodes are configured to be in electrical communication with the neural structure.

2. The method of claim 1, wherein the conduction block is a partial block.

3. The method of claim 1, wherein the one or more electrodes comprise a surface or transcutaneous electrode.

4. The method of claim 1, wherein the one or more electrodes reside in a cuff.

5. The method of claim 1, wherein the one or more electrodes comprise a percutaneous electrode.

6. The method of claim 1, wherein the one or more electrodes comprise at least one separated interface nerve electrode (SINE).

7. The method of claim 1, wherein a power required to deliver the first phase followed by the second phase of the direct current waveform is less than a power required to deliver the first phase of the direct current waveform alone over a same time period.

8. The method of claim 1, wherein the second time is greater than the first time.

9. The method of claim 1, wherein the first phase and the second phase of the direct current waveform have the same polarity.

10. The method of claim 1, where the first phase provides the conduction block of the neural structure within 1 second of delivery.

11. A system comprising:

a waveform generator configured to provide only a direct current (DC) waveform having at least two phases to one or more electrodes, wherein the DC waveform comprises:

a first phase with a first amplitude that provides a conduction block of a neural structure within 1 second, wherein the first amplitude is a block threshold value for the neural structure; and a second phase, after the first phase, with a second amplitude less than the first amplitude, but non-zero, wherein the second amplitude is a subthreshold value for the neural structure; and one or more electrodes configured to be in electrical communication with the neural structure and to:

deliver the first phase for a first time to provide the conduction block of the neural structure; and deliver the second phase for a second time, after the first time, to maintain the conduction block of the neural structure, wherein then the second phase is shut off after the second time, the recovery time of the neural structure is accelerated compared to when only the first phase is delivered.

12. The system of claim 11, wherein the one or more electrodes comprise a surface or transcutaneous electrode.

13. The system of claim 11, wherein the one or more electrodes comprise a subcutaneous electrode.

14. The system of claim 11, wherein the one or more electrodes comprise a percutaneous electrode.

15. The system of claim 11, wherein the one or more electrodes comprise at least one separated interface nerve electrode (SINE).

16. The system of claim 11, wherein the second time is greater than the first time.

17. The system of claim 11, wherein delivery of the first phase of the direct current waveform and the second phase of the direct current waveform for a time consumes less power than delivery of the first phase of the direct current waveform for the time.

18. The system of claim 11, wherein the conduction block is a partial block.

19. The system of claim 11, wherein the first phase and the second phase of the direct current waveform have the same polarity.

* * * * *